United States Patent [19]

Bloxom, Jr.

[11] Patent Number: 4,617,011

[45] Date of Patent: Oct. 14, 1986

[54] INTESTINAL IRRIGATION SYSTEM WITH FLOW INDICATOR

[76] Inventor: Ingrid B. Bloxom, Jr., P.O. Box 205, Islemorada, Fla. 33036

[21] Appl. No.: 719,175

[22] Filed: Apr. 2, 1985

Related U.S. Application Data

[63] Continuation-in-part of Ser. No. 556,036, Nov. 29, 1983, Pat. No. 4,518,382.

[51] Int. Cl.$^4$ .............................................. A61M 1/00
[52] U.S. Cl. ....................................... 604/27; 604/48; 604/73; 604/257
[58] Field of Search ................................ 604/27, 29–34, 604/48, 54, 73, 80, 246, 257, 277; 73/861.55; 340/540, 603, 605; 116/273, 276; 128/961; 200/82 E, 81.9 M

[56] References Cited

U.S. PATENT DOCUMENTS

| | | | |
|---|---|---|---|
| 2,067,474 | 1/1937 | Carbonara | 33/365 |
| 3,185,153 | 5/1965 | Leucci | 604/31 |
| 3,224,270 | 12/1965 | Karol et al. | 73/861.56 |
| 4,513,184 | 4/1985 | Hughes | 200/81.9 M |

FOREIGN PATENT DOCUMENTS 1177932  1/1970  United Kingdom .............. 200/82 E Primary Examiner—John D. Yasko
Assistant Examiner—J. L. Kruter
Attorney, Agent, or Firm—John Cyril Malloy

[57] ABSTRACT

An indicator element is movably mounted within a flow channel and is structured to travel along with and in the direction of the passage of irrigating fluid passing through the flow channel. A switching assembly is associated with the flow channel and an indicator assembly for activation of the latter wherein a predetermined position of the indicator element within the flow channel is indicative of the establishment of peristaltic action of the intestine being irrigated and of the intestine receiving adequate irrigating fluid to cause evacuation of the fecal matter contained therein. Activation of the indicator assembly informs the operator that sufficient fluid has entered the intestine to cause the peristaltic action and evacuation so that fluid flow from a fluid supply to the intestine may be stopped.

18 Claims, 6 Drawing Figures

INTESTINAL IRRIGATION SYSTEM WITH FLOW INDICATOR

This is a continuation-in-part application of co-pending application Ser. No. 556,036 filed on Nov. 29, 1983, APPARATUS FOR COLONIC AND OTHER INTESTINAL IRRIGATION, which has issued into U.S. Pat. No. 4,518,382.

BACKGROUND OF THE INVENTION

1. Field of the Invention

An intestinal irrigation and flushing system capable of determining sufficient quantity of irrigating fluid being supplied to the intestine through the detection of peristaltic action in the intestine causing reverse fluid flow from a stoma or rectum through a flow channel disposed along a path of fluid flow between the stoma or rectum and a supply of irrigating fluid. An indicator element is dimensioned and structured to travel along with and in the direction of fluid passing through the flow channel such that reverse flow resulting from peristaltic action of the intestine after sufficient quantity of fluid has been received for evacuation, forces the indicator element to an extreme position within the flow channel and serves to activate a proximity switch associated with the flow channel which in turn activates a visual and/or audible indicator assembly to warn the operator that sufficient fluid has been received in order that passages of such fluid may be stopped.

2. Description of the Prior Art

Colonic irrigation is a well known medical treatment and is utilized not only in the case of conventional enemas through the anus end of the rectum, but also in the case of irrigation through surgically provided openings into other parts of the colon. Such is the case in colostomy patients. In providing such irrigation and flushing treatment, for the purpose of evacuating fecal matter, the degree of discomfort and length of ordeal is significant.

Although varying in particular cases, the treatment has been found to be particularly disagreeable for those requiring irrigation of the intestine directly into the colon through a surgically provided stoma. Such stomas are formed from the end of a shortened colon after the end has been secured to an opening in the stomach wall and anchored to the outer skin for clear access thereto.

Equipment to introduce irrigation liquid into the colon of an ostomy patient is disclosed, for example, in U.S. Pat. No. 3,830,235 to Marsan. Such equipment conventionally includes a supply bag for irrigating liquid, a flexible tube or conduit to convey the liquid from the bag to the stoma by means of a stoma cone through which the liquid is introduced into the colon, a clip to shut off the flow through the tube, and a discharge device to catch the backflow or evacuated fecal matter when the cone is removed from the stoma. Typically, the irrigation liquid is water or water with a softening agent such as soap or other material. Such agents are disclosed, for example, in U.S. Pat. No. 4,052,986 to Scaise.

While prior equipment and systems, of the type described above, are operable to accomplish flushing and evacuation of the colon, prior art systems of this type are generally recognized, especially by patients having to undergo treatment, as having certain disadvantages. Such disadvantages relate directly to the degree of discomfort and length of time to accomplish treatment. More specifically, there is a need in the prior art to provide means to detect or determine the minimal amount of irrigating fluid to be applied to the colon, through either the stoma or rectum, to accomplish the needed evacuation of the fecal matter. In order to determine the minimal amount of fluid to be administered to the intestine, a preferred system would be structured to detect the build-up of peristaltic action of the intestine in response to injection of irrigation liquid. Such supply of irrigation liquid would be terminated when there is an indication of sufficient peristaltic action in the intestine to provide the desired evacuation without the aid of additional irrigation liquid. Such prompt termination has the further and important advantage of preventing an excessively large injection of fluid from causing a suppression of the peristaltic action originally initiated by a smaller amount of irrigation liquid initially injected.

When the injections are made in accordance with a preferred intestinal irrigation system, injection of about one-half pint or less is normally sufficient. Further, under most circumstances it is best not to exceed one pint before terminating further injection and applying a laxative preliminarily to renewing the injection the next day. Conventional irrigation systems, known in the prior art, frequently call for injection of one or two quarts of liquid. Such excessive amounts of irrigation liquid being injected into the intestine serve to suppress the peristaltic action and thereby tends to prolong the period of evacuation afterwards as well as lengthening the procedure time required to administer. All of the above greatly adds to the discomfort of the patient and in some cases can be extremely dangerous. Severe cramps, nausea, rupture of the intestine or water intoxication may occur.

SUMMARY OF THE INVENTION

The present invention is directed towards a system for colonic and other intestinal irrigation and more particularly to a flow monitoring assembly incorporated within the system and structured to visually and/or audibly indicate the existence of peristaltic action and adequate pressure in the intestine sufficient to accomplish evacuation thereof which in turn serves as a signal to stop flow of irrigating fluid into the intestine.

The system of the present invention incorporates a supply of irrigating fluid such as water which may incorporate additional softening agents or peristaltic stimulators for the purpose of allowing passage of fecal matter from the intestines being irrigated with a minimal amount of resistance. A confined path of fluid flow in the form of a conduit or flexible tubing extends from the fluid supply to an introducing means in the form of a plastic or like material stoma or rectum cone holding the distal end of the tube into direct communication with the interior of the intestine through the surgically formed stoma or rectum. It should be emphasized that reference to the details of the present invention are described with the irrigating fluid being applied to the stoma or the rectum. The system of the present invention is applicable to the evacuation of fecal matter from the intestine through either a stoma or the rectum depending upon the particular condition of the patient. Accordingly, reference to either a stoma or the rectum is not intended to limit application of the system of the present invention. A flow channel is mounted along the path of fluid flow so as to define a part thereof and comprises a tubular section structured to allow passage of irrigating fluid therethrough in either direction relative to the longitudinal axis of the flow channel.

The flow channel is maintained in a horizontal orientation which is insured by the provision of a leveling means attached thereto. An indicator element is disposed on the interior of the flow channel and may include a variety of configurations. The indicator element is specifically structured to have a specific gravity minimally greater than the specific gravity of the irrigating fluid passing therethrough. This allows total submersion of the indicator element within the fluid passing through the flow channel and further allows the indicator element to pass along with the fluid flow and in the direction thereof between opposite ends of the flow control tube. Each of these opposite ends is defined by an element seat. Each element seat is specifically structured and disposed for abutting engagement with the indicator element when it is forced into such engagement based on the flow of irrigating fluid through the flow channel. Structure of the element seats is such as to continue such flow even when abutting engagement with the indicator element has been established.

Generally, when sufficient irrigating fluid has been received by the intestine to establish evacuation of the fecal matter contained therein, a peristaltic action will develop in the intestine. Initially, as peristaltic action within the intestine develops, intestinal fluid pressure will reverse slightly several times. The flow of irrigating liquid therefore temporarily stops due to a slight back pressure, caused by the initiation of peristaltic action, and then flow resumes to the intestine. However, when sufficient peristaltic action has developed, sufficient intestinal fluid pressure will be created to cause evacuation of fecal matter and a reverse fluid flow of the irrigating fluid entering the stoma or rectum. Such reverse fluid flow will be sufficient, when the peristaltic action is sufficient, to force the indicator element along therewith. The indicator element is thereby seated or at least positioned in close proximity to the element seat at an end of the flow channel tube associated closest to the supply of irrigating fluid relative to the length of the path of fluid flow.

The monitoring assembly of the present invention incorporates what may generally be referred to as two proximity switches each of which are disposed adjacent to an opposite longitudinal end of the flow channel. Such proximity switches are structured in cooperation with the indicator element such that these switches may be activated or closed upon the indicator element being positioned in close proximity thereto. Further, the individual proximity switches are disposed in circuitry to interconnect a visual and/or audible indicating signal defining an indicator assembly, with a power supply such as a d.c. battery or other conventional source of electric power. When either of the proximity switches is activated due to close proximity of the indicator element therewith, the proper indicator signal is activated or deactivated informing the operator of the system as to the location of the indicator element within the flow channel and therefore the direction of fluid flow and accordingly the existence and/or degree of peristaltic action of the intestine.

As set forth above, when sufficient peristaltic action has been developed in the intestine to accomplish evacuation, the resulting reverse fluid flow from the intestine through the flow channel serves to force the indicator element to the opposite or far end of the flow control tube and in close proximity to a designated one of the two proximity switches. Such close proximity serves to activate the designated proximity switch and in turn activate the proper indicator signal. The operator, upon receiving such signal, is informed that sufficient irrigation liquid has been supplied to the intestine, through the stoma or rectum to accomplish peristaltic action, and therefore evacuation, and injection of additional irrigating fluid is stopped.

BRIEF DESCRIPTION OF THE DRAWINGS

For a fuller understanding of the nature and structure of the present invention, reference is had to the following detailed description taken in connection with the accompanying drawings, in which.

Like reference numerals refer to like parts throughout the several views of the drawings.

DETAILED DESCRIPTION OF THE PREFERRED EMBODIMENT

Figure 1:
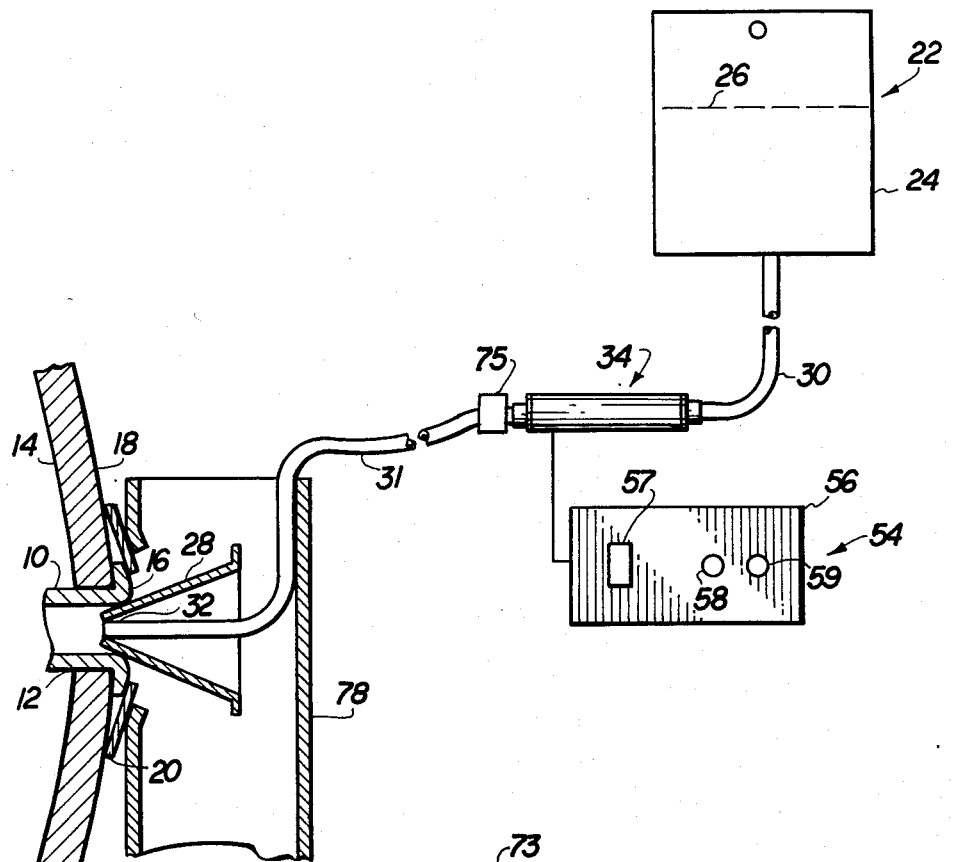
FIG. 1 is a schematic representation in partial section showing the various components of the system in proper position and operation to accomplish supply of irrigation fluid to a stoma of the intestines.

With reference to FIG. 1, the system of the present invention is directed to the irrigation or flushing of intestine 10 surgically secured to an opening 12 in the wall of the stomach or like body portion 14. The intestine 10 is secured thereto by a surgically formed stoma 16 secured to the outer surface 18 of the body wall 14 in any conventional manner such as by a retaining sleeve or member 20. It should be emphasized that the system of the present invention is not limited to application to colostomy patients wherein the irrigating fluid is applied through a surgically formed stoma 16. Rather, the present system has great versatility and is applicable for use when irrigating fluid is applied to the intestines directly through the rectum or other location structured for fluid flow to and from the intestine.

The system is schematically represented in FIG. 1 and includes a supply of irrigating fluid generally indicated as 22 wherein such irrigating fluid may be water with or without softening agents, such as soaps or other materials, added thereto. The fluid supply 22 may be a conventional bag or any container 24 holding the irrigating fluid 26 in a position such that it is supplied by gravity to an introducing means in the form of an introducing cone 28. It is important to note that the cone must be secured or applied to the stoma 16, rectum or other body opening, for introduction of fluid into the intestine 10 such that back pressure or any force resulting from reverse flow will not serve to inadvertently dislodge or remove the cone 28 or cause leakage around the intersecting surfaces thereof.

Figures 3, 4:
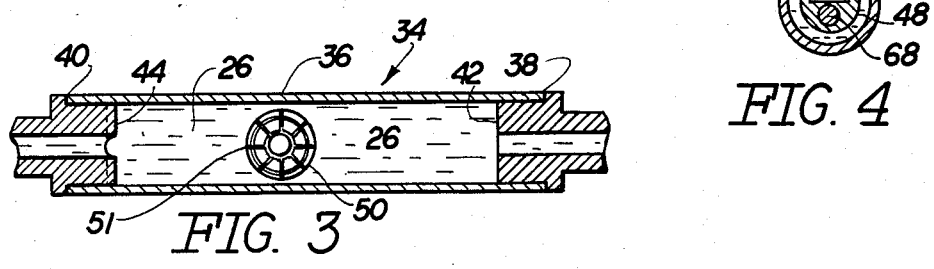
FIG. 3 is a sectional view of one embodiment of the indicator element mounted within the flow control of the present invention.
FIG. 4 is a sectional view along line 4—4 of FIG. 2 showing another embodiment of the indicator element of the present invention.

The system of the present invention further comprises a path of fluid flow defined by a flexible or like material conduit 30 and 31 wherein the distal end as at 32 of conduit portion 31 is secured or otherwise introduced into the cone 28 so as to provide fluid directly through the opening 16 into the intestine 10. The positioning of distal end 32 should also be such as to receive reverse fluid flow from the intestine back through conduit 31 when peristaltic action is developed in the intestine 10, as will be described in greater detail hereinafter. The path of fluid flow further includes a flow channel generally indicated as 34 in the form of a generally elongated tube 36 connected at opposite ends 38 and 40 to conduit portions 30 and 31. The flow channel conduit or tube 36 thereby defines a part of the path of fluid flow and is specifically structured to allow the irrigating fluid 26 to pass therethrough. Further, each of the opposite ends 38 and 40 are defined by an element seat structure 42 and 44 respectively wherein at least one of such element seats, such as 44, has a grooved or recess cut configuration. An indicator element 48 is mounted within the interior of the flow channel conduit 36 and specifically structured to pass along the length thereof between the opposite ends 38 and 40. Travel or movement of the indicator element 48 is caused by the flow of fluid 26 through the flow channel conduit 36. This is accomplished by virtue of the fact that the indicator element 48 is specifically structured to have a specific gravity at least minimally greater than the specific gravity of the fluid 26. This allows complete submersion of the indicator element therein while at the same time forcing movement of the indicator element 48 along with and in the direction of the travel of fluid through the conduit. As best shown in FIG. 4, one embodiment of the indicator element 48 includes an air chamber 49 formed therein so as to regulate the overall weight thereof regardless of the configuration and dimension. This weight regulating serves in turn to maintain the specific gravity of the indicator element in the preferred range of being at least minimally greater than in the specific gravity of the irrigating fluid 26.

Accordingly, when the irrigating fluid 26 travels from the fluid supply 22 through the respective conduits 30 and 31 and into the intestine 10 through opening 16, the direction of travel of the fluid through the flow channel is towards the opening 16 and away from the fluid supply 22. The indicator element 48 is forced into substantially abutting engagement with the element seat 44 as represented in broken lines as 48'. Due to the grooved or recessed cut configuration of the element seat 44, passage of fluid is still allowed to flow through the seat 44 and into the conduit portion 31 to the opening 16 which may be a stoma or rectum.

However, upon the development of peristaltic action within the intestine 10, evacuating pressure is created therein which forces the irrigating fluid 26 into a reverse direction of flow from the intestine 10 through the opening 16 and introducing cone 28 and back through conduit portion 31. If the peristaltic action in the intestine is sufficient to accomplish the required evacuation of fecal matter, the reverse flow of irrigating fluid 26 will continue through the flow channel conduit 36 and force the indicator element 48 to the opposite end 38 of the flow channel conduit 36 and into abutting relation with the element seat 42 as indicated by broken lines as 48". Therefore, it is readily seen that when the indicator element 48 is forced into close proximity with the opposite end 42 of the flow control conduit 36, sufficient peristaltic action has been developed and further supplying of irrigating fluid 26 to the intestine 10 through the stoma or rectum opening 16 is not required but in fact derrogatorily affects proper flushing of the intestine 10. It is therefore important that once sufficient peristaltic action has been developed in the intestine 10 that further feeding or injection of irrigating fluid 26 into the intestine must be stopped.

Accordingly, an important feature of the present invention is the provision of a flow monitoring assembly generally indicated as 54. Such assembly includes a certain portion housed within a casing 56 (see FIG. 1) and includes an on/off switch 57 and at least a first and second visual indicator portion such as signal lamps 58 and 59. These lamps define a portion of an indicator assembly which may further include an audible signal such as a buzzer 60 or like audible alarm electrically interconnected in parallel to at least one of the signal lamps 59. The monitoring means further includes an indicator sensing means generally indicated as 62 and including, in a preferred embodiment, a first proximity switch 64 and a second proximity switch 66. The first proximity switch 64 includes sensing contacts 65 mounted adjacent to and in direct proximity with opposite ends 38 and element seat 42 of the flow channel conduit 36. Similarly, the second switch 66 includes contacts 67 disposed adjacent to and in direct proximity with end 40 and seat 44 of the flow channel conduit 36. Each of the first and second switches are specifically structured to be activated or closed to complete additional circuitry, set forth hereinafter, upon indicating the presence or close proximity of a magnet 68 which is attached to the indicator element 48.

Figure 2:
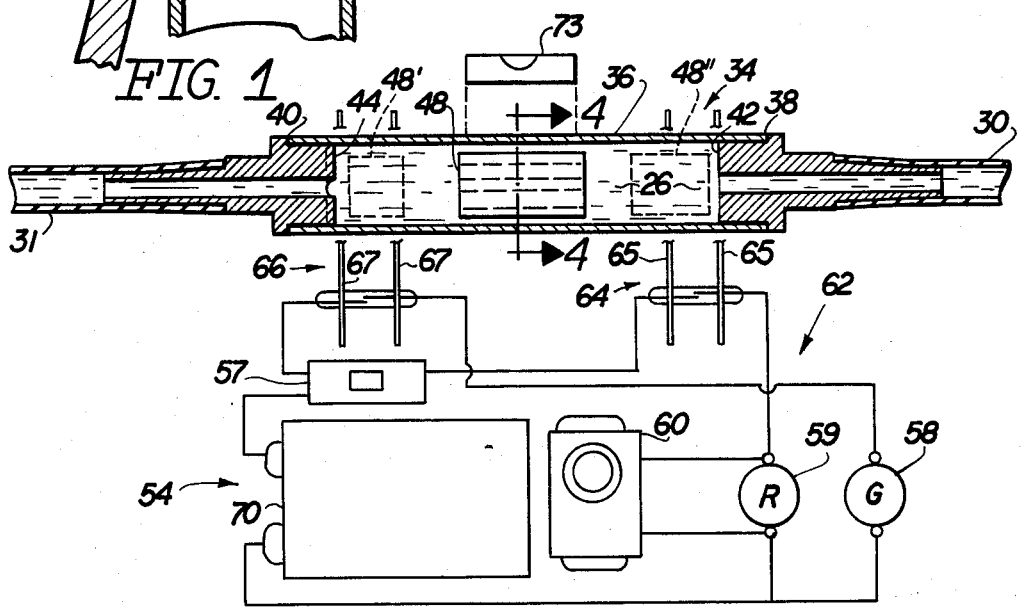
FIG. 2 is a sectional view and in partial schematic showing structural details of a flow control portion of the system and a schematic of the circuitry of a flow monitoring assembly thereof.

With regard to FIG. 2, the monitoring means 54 further includes an electrical power supply being interconnected to both signal lamps 59 and 58 through first and second switches 64 and 66 respectively. It is readily apparent therefore that when either of the switches 64 or 66 is closed due to sensing the close proximity of the indicator element 48 and particularly carrying magnet 68, a circuit will be completed between the electrical power supply 70 and the respective signal lamp 59 and 58 and/or audible signal 60.

In operation, initial injection or supply of irrigating fluid from the fluid supply 22 through respective conduit portions 30 and 31 and through flow channel 34 causes indicator element 48 to travel the length of the flow channel conduit 36 and into abutting engagement with or close proximity to opposite end 40 and a second of two element seats 44. When the indicator element 48 is in the position indicated in broken lines as 48', the second proximity switch 66 will be activated or closed thereby completing the circuit between signal lamp 58 and the power supply 70. Lamp 58 may be a green signal indicating proper flow of irrigating fluid is taking place into the intestine 10 through stoma or rectum opening 16. Upon the initiation of peristaltic action in the intestine, fluid pressure therein will begin to fluctuate or reverse slightly several times. This causes the flow of incoming irrigating fluid to be temporarily stopped due to a slight back pressure. Thereafter, the inflow of irrigating fluid resumes into the intestine. This initial and slight fluctuation in fluid flow causes the indicator element 48 to back-off a small distance from its engagement with seat 44 and vary its proximity relative to the contacts 67 of proximity switch 66. This small fluctuation in the positioning of indicator element 48, as it varies slightly in its absolute position 48' relative to the contacts 67, will cause an on-off blinking or "fluttering" of indicator light 58. This will in turn indicate to the user of the system that peristaltic action in the intestine has been initiated but is not yet sufficient to create the required intestinal fluid pressure necessary to accomplish evacuation of the fecal matter therefrom. However, when sufficient peristaltic action takes place within the intestine 10, a consistent reverse fluid flow will occur through the intestine 10, out of stoma or rectum opening 16, beyond distal end 32 of conduit portion 31 and into the flow channel conduit 36. Such reverse flow will cause the indicator element 48 to be positioned into abutting relation or at least close proximity to element seat 42 as indicated by broken lines 48". Such close proximity of indicator element 48 to the contacts 65 of the first switch 64 will cause the red light or signal lamp 59 to be activated and/or audible signal 60 to be activated through interconnection of the electrical supply 70 therewith. Activation of signal elements 59 and/or 60 indicates to the operator of the system that sufficient peristaltic action and intestinal fluid pressure have been established to accomplish evacuation of fecal matter from the intestine. The operator can therefore cease all supply of irrigating fluid from the fluid supply 22 by a flow regulating means 75 in the form of a shut-off valve or like element. The introducing cone 28 is thereby removed and evacuation of fecal matter and irrigating fluid is allowed to be emptied through stoma or rectum opening 16 into a receiving facility 78.

Another structural feature of the present invention is clearly shown in FIG. 4 wherein the indicator element 50 is in the form of a ball or sphere instead of the elongated configuration as described with reference to the embodiment of FIG. 2. Further, the exterior surface of indicator ball 50 is cut, grooved or generally formed to be inconsistent so as to provide traction and a certain amount of resistance to the interior surface of the flow channel conduit 36 thereby facilitating travel of the indicator element along the length of the conduit 36 in a positive manner, dependent upon the direction of fluid flow therethrough.

Figure 5:
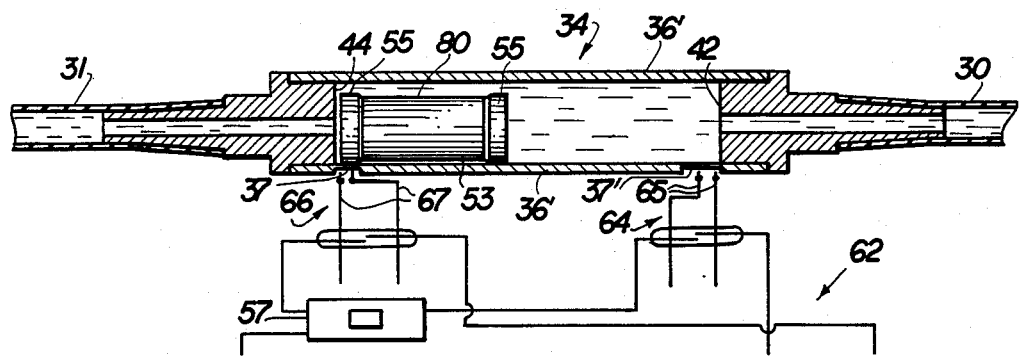
FIG. 5 is a sectional view in partial schematic showing structural details of another embodiment of a flow control portion of the system and the associated switching portion of the associated circuitry of a flow monitoring assembly thereof.
Figure 6:
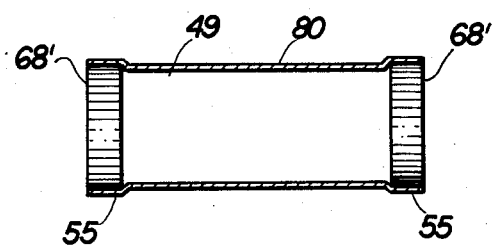
FIG. 6 is a detail view of another embodiment of the indicator element associated with the flow control portion of the present invention.

With primary reference to FIGS. 5 and 6, an additional embodiment of the present invention comprises the flow conduit or tube 36 having a substantially thickened wall 36' and sensing windows 37 and 37' integrally formed in at least a portion of the outer wall 36' generally in the area of the seats 44 and 42 located at the opposite ends of the flow conduit 36. A flow indicator element 80 includes magnets 68' formed in opposite ends thereof. The magnets are dimensioned so as to be capable of being press-fitted or otherwise secured within the opposite extremities of the indicator element as clearly shown in FIG. 6. Such press-fitting interconnection of these magnets 68' causes an outward flaring or enlargement of the opposite extremities as at 55. Accordingly, when the indicator element 80 travels in either direction on the interior of flow conduit 36', only the outwardly flared or enlarged end portions 55 serve to engage the interior surface of the conduit 36 during such sliding travel. Frictional resistance between the interior surface and the indicator element 80 is thereby reduced and a more accurate indication of the direction of fluid flow through the conduit 36 is provided since less resistance to travel is applied against the entire outer surface of the indicator element 80. With reference to FIG. 5, it is clear that a spacing 53 exists along a major portion of the length of the indicator element and between the enlarged or outwardly flared end portions 58 which surround the magnets 68'.

As set forth above, the respective proximity switches 64 and 66 are activated when the indicator element 80 and the respective magnets 68' which it carries passes into the field of influence of the respective contacts 65 and 67 of the proximity switches 64 and 66. In order to increase the sensitivity of the subject system, windows 37 and 37' in the form of integrally formed recesses are disposed in the thickened outer wall 36' of the conduit 36 in order to place the individual contacts, as shown in FIG. 5, in directly adjacent position relative to the positions the respective magnets 68' will assume when the indicator element 80 is associated with the respective seats 44 and 42. It should be emphasized that the term "window" is not meant to imply or denote a transparent structure but rather a section of wall of conduit 36 having a reduced thickness. Therefore, individual contacts 67 are disposed within or immediately adjacent to window 37 so as to be placed directly within the field of influence of the magnetic field created by the presence of one of the magnets 68' associated with the end of the indicator element 80 disposed in abutting or adjacent relation to the seat 44. Similarly, at the opposite end of the conduit 36 a somewhat larger winder 37' is provided in direct receiving relation to or adjacent the contacts 65 of the proximity switch 64. The length of the window 37' is somewhat longer than that of the window 37 so that the magnet 68' associated with the end of indicator element 80 disposed adjacent to or in abutting relation with the seat 42 will more quickly influence and/or activate the contacts 65 and the proximity switch 64 as the respective magnet 68' approaches and eventually is seated in abutting engagement with or adjacent to the seat 42. Accordingly, and as set forth above, the forced travel of indicator element 80 into adjacent relation to the seat 42 indicates that sufficient peristaltic action has occurred to create adequate fluid pressure to cause evacuation of the intestine. Approaching of the respective magnet 68' of indicator element 80 will serve to more quickly activate proximity switch 64 due to the enlargement of the window 37' thereby causing an activation of the signal lamp 59 and/or audible buzzer 60. Irrigating fluid may then be stopped by the operator of the system based on this indication of adequate peristaltic action and intestinal fluid pressure as well as impending evacuation of any fecal matter contained within the intestine.

Other structural features of the present invention include the provision of a leveling means 73 mounted on the flow channel 34 so as to move therewith (FIG. 2). The leveling means 73 is particularly structured and disposed to indicate the true level orientation of the flow channel conduit 36 relative to horizontal in order that movement or travel of the indicator element 48 is not unnecessarily biased or influenced by gravity but is totally reliant upon direction of fluid flow 26 through the flow channel conduit 36.

What is claimed is:

1. An apparatus for controlled intestinal irrigation and monitoring comprising:
  (a) a container means for supply and storage of irrigating fluid,
  (b) introduction means positionable adjacent to and in fluid delivering relation with an entrance to an intestine being irrigated for introducing liquid thereto, (c) conduit means disposed in interconnecting and fluid communicating relation between said container means and said introduction means for defining a path of liquid flow therebetween, (d) flow regulating means connected to said conduit means and structured and disposed to stop and control liquid flow from said container means to said introduction means, whereby flow of irrigating fluids to the intestine is selectively stopped by said flow regulating means upon an indication of peristaltic action of the intestine by a flow indicator, (e) a flow indicator means including a flow channel for indicating direction of fluid flow within said conduit means, said flow channel connected to said conduit means between said container means and said introduction means, said flow channel structured to accommodate liquid flow therethrough from said container means to the intestine and reversely from the intestine into said flow indicator means, (f) said flow indicator means including an indicator element movably disposed therein and within liquid flow passing therethrough, (g) said flow channel comprising opposite ends each of which including an element seat disposed for abutting engagement with said indicator element and comprising a flow through construction to maintain said indicator element out of fluid sealing engagement therewith, (h) said indicator element means cooperatively structured and disposed relative to said flow channel for responsive longitudinal displacement therein based on peristaltic action of the intestine during flow of liquid through said flow indicator means to the intestine, (i) a monitoring means for determining direction of fluid flow through said flow channel into and out of said introduction means and including an indicator sensing means mounted adjacent said flow channel and structured for sensing the position of said indicator element within said flow channel, (j) said sensing means further structured and disposed for electrical interconnection of a power supply to an indicator assembly and actuation of said indicator assembly dependent upon said positioning of said indicator element within said flow channel relative to said sensing means, (k) said indicator element including activating means thereon bring structured for activation of said indicator sensing means when in proximity thereof, (l) whereby flow of irrigating liquid to the intestine is selectively stopped by said flow regulating means upon the development of peristaltic action of the intestine indicated by travel and positioning of said indicator element based on direction of fluid flow through said flow channel in a direction from said introduction means.

2. The system of claim 1 wherein said indicator sensing means comprises at least a first switch disposed adjacent one of said opposite ends of said flow channel and structured in cooperation with said indicator element, to complete electrical connection between the power supply and said indicator assembly upon said indicator element being disposed in close proximity to said first switch.

3. The system as in claim 2 wherein said first switch is disposed adjacent said one opposite end located closest to said supply of irrigating fluid along said path of fluid flow, said indicator element structured to travel substantially the length of said flow channel and into abutting engagement with said respective seat associated with said first switch and along with and in the direction of fluid flow from the stoma through said flow channel due to peristaltic action of the intestine, whereby activation of said indicator assembly is indicative of said peristaltic action and a need to stop passage of fluid from said supply of irrigating fluid to the stoma.

4. The system as in claim 2 wherein said sensing means comprises at least a second switch disposed adjacent the other of said opposite ends of said flow channel and structured for actuation by close proximity of said indicator element, said first and said second switches each independently structured for electrical interconnection of the electric power supply and said indicator assembly and each independently actuatable for respective actuation of said indicator assembly through said electrical interconnection upon disposition of said indicator element in close proximity to respective element seats.

5. The system as in claim 4 wherein said indicator element is structured to travel the length of said flow channel and into close proximity to a first of said element seats associated with said first switch and a second of said element seats associated with said second switch dependent on flow of fluid traveling along said path of fluid flow from the stoma through said flow channel; and from said supply of irrigating fluid to the stoma, respectively; said flow of fluid from the stoma through said flow channel due to peristaltic action of the intestine, whereby activation of said indicator assembly by said first switch is indicative of stopping the passage of fluid along said path of fluid flow by said regulating means.

6. The system as in claim 4 wherein said first switch and said second switch further comprise a magnetic actuated switch assembly mounted adjacent to respective opposite ends associated with said first switch and said second switch, said indicator element comprising a magnet mounted thereon and being structured to travel the length of said flow channel and into close proximity to either opposite end thereof and into abutting engagement with said respective element seats associated with each of said opposite ends and said first switch and second switch respectively associated with said opposite ends along with and in the direction of a flow of fluid traveling through said flow channel.

7. The system as in claim 4 wherein said indicator assembly comprises a first visual indicator and a second visual indicator each interconnected to the electric power supply and thereby activated by said first switch and said second switch respectively upon said indicator element being disposed by fluid flow within said flow channel into close proximity with associated ones of said element seats.

8. The system as in claim 7 wherein said indicator assembly further comprises an audible indicator connected to said first visual indicator for simultaneous activation therewith by said first switch.

9. The system as in claim 2 wherein said first switch comprises a magnetic actuated switch assembly mounted adjacent to said one opposite end of said flow channel, said indicator element comprising a magnet mounted thereon, said indicator element structured to travel into close proximity to said one opposite end, said element seat associated therewith and said first switch upon flow of fluid from the stoma to said flow channel due to peristaltic action of the intestine.

10. The system as in claim 6 wherein said indicator element further comprises an air chamber formed therein and dimensioned and configured to at least partially define the specific gravity of said indicator element being minimally greater than the specific gravity of the irrigating fluid traveling through said flow channel.

11. The system as in claim 7 wherein said indicator element comprises a substantially spehercial configuration having an outer surface structured to be inconsistent and thereby provide at least a minimal resistance to interior surface portions of said flow channel and said respective element seats.

12. The system as in claim 11 wherein said indicator element includes an air chamber formed therein and being dimensioned to at least partially define the specific gravity thereof being minimally greater than the specific gravity of the irrigating fluid.

13. The system as in claim 1 further comprising a level indication means mounted on said flow channel so as to move therewith and being structured to indicate position of said flow channel relative to a true horizontal orientation.

14. The system as in claim 1 wherein said indicator sensing means comprises a first and a second magnetically actuated switch assembly each mounted adjacent an opposite end of said flow channel and said indicator element comprising a magnet formed therein, each switch assembly including contact means for sensing a magnet in close proximity thereof; said flow channel comprising a conduit including an enclosing barrier wall disposed in surrounding relation to the interior of said conduit, a sensing window integrally formed in said barrier wall at each of the opposite ends of said conduit, each of said sensing windows disposed adjacent respectively positioned element seats and each comprising a recessed portion defining a reduced thickness barrier wall section, said contact means of each switch assembly mounted directly adjacent one of said sensing windows and thereby in close proximity to said indicator element when the latter is disposed adjacent a respective element seat.

15. The system as in claim 14 wherein at least one sensing window has an enlarged length relative to the other and is dimensioned and configured for placement of correspondingly positioned contacts of one of said switch assemblies in actuating position to said indicator element when the latter is approaching said correspondingly positioned element seat.

16. The system as in claim 1 wherein said indicator element comprises a magnet fixedly secured to each opposite end thereof and each magnet being diametrically greater in dimension than the diameter of said flow control channel and each disposed to flare outwardly from the remaining portion of said flow control channel disposed between said oppositely disposed magnets, said remaining portion disposed out of engagement with interior surface portions of said flow control channel when said indicator element travels along the length thereof.

17. In an intestinal irrigation and flushing system of the type including a supply of irrigating fluid in a path of fluid flow interconnecting and establishing a flow of fluid between said fluid supply an a means to introduce a fluid to a body opening communicating with the intestine, said system being indicative of reverse fluid flow from the intestine and through the body opening and along said path of fluid flow due to peristaltic action of the intestine, said system including flow regulating means for starting and stopping fluid flow along said path of travel between said supply and said introducing means; an improvement comprising a flow monitoring assembly which includes:

(a) a flow channel disposed in fluid communication with said path of fluid flow in interconnecting relation between said supply and said introduction means and structured to direct irrigating fluid therethrough, (b) an indicator element disposed within said flow channel and structured to travel along the length thereof in the direction of and with fluid flow therethrough and between opposite ends of said flow channel, said indicator element further comprising an air chamber formed therein and dimensioned and configured to at least partially define the specific gravity of said indicator element as being minimally greater than the specific gravity of the irrigating fluid traveling along said path of fluid flow, (c) each opposite end of said flow channel comprising an element seat disposed for abutting engagement with said indicator element and comprising a flow through construction to maintain said indicator element out of fluid sealing engagement therewith, (d) a monitoring means for determining direction of fluid flow through said flow channel into and out of the body opening and including an indicator sensing means mounted adjacent said flow channel and structured for sensing the position of said indicator element within said flow channel, (e) said sensing means further structured and disposed for electrical interconnection of a power supply to an indicator assembly and acutation of said indicator assembly dependent upon positioning of said indicator element within said flow channel relative to said sensing means, and (f) said indicator element including activation means thereon being structured for activation of said indicator sensing means when in the proximity thereof, whereby position and travel of said indicator element based on direction of fluid flow through said flow channel is determined by activation of said indicator assembly.

18. In an intestinal irrigation and flusing system of the type including a supply of irrigating fluid and a path of fluid flow interconnecting and establishing a flow of fluid between said fluid supply and a means to introduce the fluid to a body opening communicating with the intestine, said system being indicative of reverse fluid flow from the intestine and through the body opening and along said path of fluid flow due to peristaltic action of the intestine, said system including flow regulating means for starting and stopping fluid flow along said path of travel between said supply and said introducing means; and improvement comprising a flow monitoring assembly which includes:

(a) a flow channel disposed in fluid communication with said path of fluid flow in interconnecting relation between said supply and said introducing means and structured to direct irrigating fluid therethrough, (b) an indicator element disposed within said flow channel and structured to travel along the length thereof in the direction of and with fluid flow therethrough and between opposite ends of said flow channel, (c) each opposite end of said flow channel comprising an element seat disposed for abutting engagement with said indicator element and comprising a flow through construction structured to maintain said indicator element out of fluid sealing engagement therewith, (d) a monitoring means for determining direction of fluid flow through said flow channel into and out of the body opening and including an indicator sensing means mounted adjacent said flow channel and structured for sensing the position of said indicator element within said flow channel, (e) said sensing means further structured and disposed for electrical interconnection of a power supply to an indicator assembly and actuation of said indicator assembly dependent upon positioning of said indicator element within said flow channel relative to said sensing means, (f) said indicator sensing means comprising a first and a second magnetically actuated switch assembly each mounted adjacent an opposite end of said flow channel and said indicator element comprising a magnet formed therein, each switch assembly including contact means for sensing a magnet in close proximity thereto, (g) said flow channel comprising a conduit including an enclosing barrier wall disposed in surrounding relation to the interior of said conduit, a sensing window integrally formed in said barrier wall at each of the opposite ends of said conduit, each of said sensing windows disposed adjacent respectively positioned element seats and each comprising a recess portion defining a reduced thickness barrier wall section, (h) said contact means of each switch assembly mounted directly adjacent one of said sensing windows and thereby in close proximity to said indicator element when the latter is disposed adjacent a respective element seat, (i) whereby position and travel of said indicator element based on direction of fluid flow through said flow channel is determined by activation of said indicator assembly.

* * * * *